United States Patent [19]
Garner

[11] Patent Number: 5,104,218
[45] Date of Patent: * Apr. 14, 1992

[54] MICROPIPETTE ADAPTOR FOR SPECTROFLUORIMETERS

[75] Inventor: Harold R. Garner, Encinitas, Calif.

[73] Assignee: General Atomics, San Diego, Calif.

[*] Notice: The portion of the term of this patent subsequent to Feb. 12, 2008 has been disclaimed.

[21] Appl. No.: 433,752

[22] Filed: Nov. 9, 1989

[51] Int. Cl.⁵ .................. G01N 21/64; G01N 21/03
[52] U.S. Cl. .................... 356/73; 250/576; 356/244; 422/52
[58] Field of Search ............... 422/99, 100, 62; 356/244, 246, 73; 250/576

[56] References Cited
U.S. PATENT DOCUMENTS 3,920,334 11/1975 Steichen et al. ............ 356/73
4,008,397 2/1977 Zdrodowski ............. 356/246 X
4,475,813 10/1984 Munk ................... 356/73
4,991,958 2/1991 Garner ................. 356/244

Primary Examiner—Vincent P. McGraw
Attorney, Agent, or Firm—Nydegger & Associates

[57] ABSTRACT

An adaptor for holding a micropipette in a spectrofluorimeter includes a base member for holding the micropipette and an optical system for linearly focusing visible or ultraviolet light onto a sample solution held in the micropipette. Specifically, the optical system includes a cylindrical lens which focuses collimated light from a light source into a line along the axis of the micropipette. The optical system also includes a cylindrical quartz lens which recollimates the light that emerges from the micropipette sample holder in a direction which is perpendicular to the direction of the incident light. A spectrometer is provided to receive the recollimated light for measuring the light absorption and light emission characteristics of the sample material held in the micropipette.

32 Claims, 2 Drawing Sheets

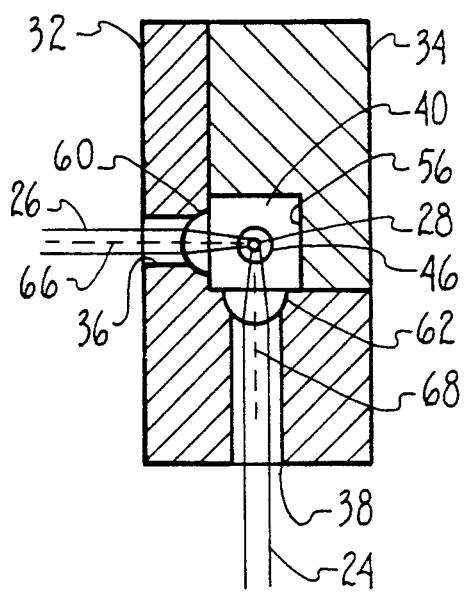
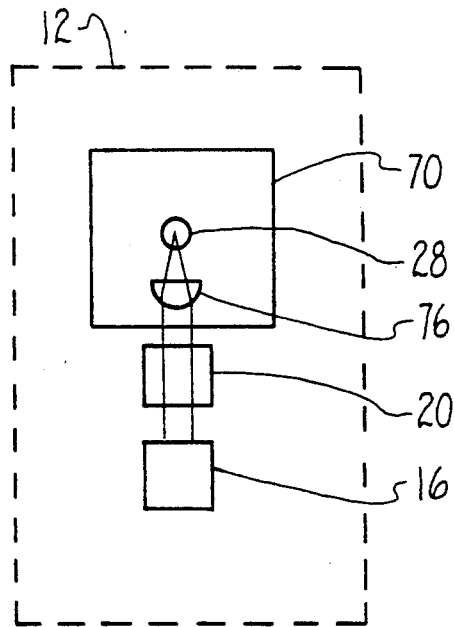
Fig. 4          Fig. 5
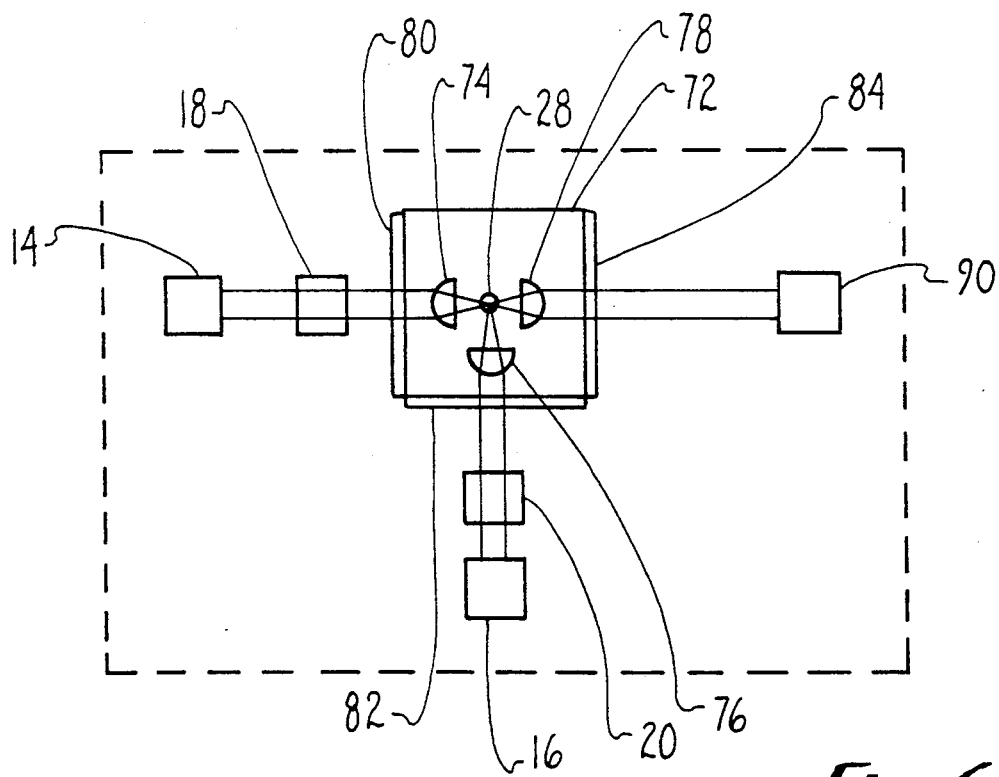
Fig. 6

MICROPIPETTE ADAPTOR FOR SPECTROFLUORIMETERS

FIELD OF THE INVENTION

The present invention pertains to devices which hold solutions of sample materials while the composition of the material is being measured and analyzed. Specifically, the present invention pertains to sample holders which may be used with spectrofluorimeters and spectrophotometers. The present invention is particularly, but not exclusively, useful for obtaining spectroscopic measurements of very small samples of material.

BACKGROUND OF THE INVENTION

The use of spectrophotometers and spectrofluorimeters to measure the light absorption and emission characteristics of sample materials is well known. Indeed, the basic principles involved are relatively simple. A beam of light, whose characteristics are known, is directed through the sample material and the light that emerges is analyzed to determine which wavelengths of the original beam were absorbed or absorbed and emitted at another wavelength, or otherwise affected, by the sample material. Based on differences between the incident light and the transmitted or emitted light, certain characteristics of the sample material can be determined. The processes of spectrophotometry and spectrofluorimetry, however, while related, proceed from fundamentally different physical principles. Stated simply, spectrophotometry measures the effect the sample material has on the incident beam, whereas spectrofluorimetry measures the effect the incident beam has on the sample material. More particularly, both processes recognize the well-known quantum physics principle that molecules or atoms which are in one quantum energy state may absorb incident photons having particular wavelengths, and thereby be excited into a higher quantum energy state. The now-excited molecule or atom will tend to revert to its ground quantum energy state, either by thermally losing its excitation energy to its surrounding environs or, alternatively, by emitting one or more photons. In the latter case, when emission of the photon is from a singlet quantum state, the process is known as fluorescence. On the other hand, if the photon emission is from a triplet state, the process is known as phosphorescence. Moreover, as is well known, the wavelength of the emitted photon must have a longer wavelength (i.e., less energy) than the incident exciting photon. In its simplest terms, spectrophotometry determines certain sample characteristics by measuring the total amount of incident light which is absorbed, without considering how the absorbing molecules revert back to their ground quantum state. In contrast, spectrofluorimetry determines certain sample characteristics by measuring the fluorescent or phosphorescent properties of a specimen through which light has been directed, to determine certain specimen characteristics. Additionally, the principles underlying spectrofluorimetry may be applied to determine certain characteristics of chemiluminescent and bioluminescent samples. Samples in this genre of material spontaneously emit photons, and hence do not require irradiation with excitation photons in order to induce emission of photons. The principles of sample analysis and evaluation, however, remain unchanged. It will therefore be appreciated that a single spectrofluorimetry device may potentially provide for sample analysis by either exciting sample molecules with external radiation, or by observing the spontaneous photon emission of chemiluminescent or bioluminescent samples.

There is a problem with the above analytic procedures, however, when high solutions of sample material are available in only very small quantities (e.g. 0.5 to 50 micrograms/microliter).

To be effective for spectroscopic measurements, test cuvettes for holding the sample material must be completely filled. This typically requires a substantial amount of sample material or a dilution of the sample material. Consequently, when only a small amount of the sample material is effectively available for testing or if it is desired not to dilute the sample thus ruining it for follow on use, presently available test cuvettes (e.g. 12.5 mm × 12.5 mm cuvette) are inadequate because of their relatively large size. Merely reducing the size of the cuvette is not the answer. This is so because, with a size reduction of the cuvette, there is also a reduction in the amount of sample material through which light can pass. Consequently, the intensity of the light passing through the sample material is reduced and the sensitivity and accuracy of the measurement is compromised.

The present invention recognizes that it is possible to take spectrofluorescent and spectrophotometric measurements of very small quantities of a sample material, even where there is a relatively high concentration of the material in solution. The present invention recognizes that this can be done by properly focussing collimated light onto the sample material to obtain sufficiently high input light intensities for the desired measurements. Further, the present invention recognizes that this focussing can be accomplished by a device which is engageable, and operatively compatible, with presently available spectrofluorimeters such as the LS-50 Luminescence Spectrometer by Perkin Elmin, or spectrophotometers such as a UVIKON Model 820 spectrophotometer by Kontron.

In light of the above, it is an object of the present invention to provide a micropipette adaptor for spectrographic analysis which allows for spectrofluorescent or spectrophotometric measurements of very small quantities of sample material in solution. Another object of the present invention is to provide a micropipette adaptor for spectrographic analysis which permits recovery of the sample material after spectrographic measurements have been made. Yet another object of the present invention is to provide a micropipette adaptor for spectrographic analysis which allows spectroscopic measurements of samples to be made while the sample is in the process of being transferred in a micropipette. Still another object of the present invention is to provide a micropipette adaptor for spectrographic analysis which provides for a high light collection efficiency to increase the sensitivity of the measurements which are made. Another object of the present invention is to provide a micropipette adaptor for spectrographic analysis which allows a micropipette or other capillary sample holder to be easily installed and removed from the adaptor.

SUMMARY OF THE INVENTION

The micropipette adaptor for spectrofluorimeters according to the present invention comprises a base member that is adapted to hold a capillary tube, such as a micropipette, which is filled with a solution of the sample material to be analyzed. More specifically, the base member is formed with an opening, and is formed with a hole which is distanced across the opening from a conical well. As formed on the base member, both the hole and the conical well are aligned with each other to respectively receive a portion of the micropipette and hold it on the base member. When so held, the micropipette extends across the opening of the base member.

An optical system is provided for the adaptor and is attached to the base member to focus a beam of collimated light through the opening and onto the micropipette, and to then collimate the light that fluoresces from the micropipette. For focussing the beam of collimated light onto the micropipette, a cylindrical quartz lens (i.e. a directing lens) is positioned between the base member and the source of collimated visual infrared or ultraviolet light. Specifically, this directing lens is used to focus collimated light from the light source into a line. In accordance with the present invention, this linearly focused light is aligned along the longitudinal axis of the micropipette to provide a very high intensity light input for the sample material which fills the lumen of the micropipette. Another cylindrical quarts lens (i.e. a receiving lens) is positioned with its focal axis at a substantially right angle to the focal axis of the directing lens to receive the light which fluoresces from the sample material in the pipette and to recollimate if for analysis and measurement by a detector. It will be appreciated by the skilled artisan that, depending on the wavelength of the light, the receiving lens and the directing lens may be made of quartz, glass, sapphire, fused silica or any other appropriate light transmitting material.

As contemplated by the present invention, the adaptor is intended for use with very small micropipettes. For example, it is within the contemplation of the present invention that a micropipette having a capillary tube with a lumen which is approximately half a millimeter (0.5 mm) in diameter can be effectively used with the adaptor disclosed herein. Even so, it will be appreciated by the skilled artisan that pipettes of various sizes may be used. Furthermore, it is to be appreciated that the light wavelengths which are useful with the adaptor of the present invention need not necessarily be limited to the visual and ultraviolet ranges.

The adaptor is preferably made to absorb light (i.e. is colored black) in order to minimize the amount of direct light from the light source that is received by the detector. Further, in an alternate embodiment for the present invention, when chemiluminescent or bioluminescent materials are to be analyzed, the light source and the directing lens may be eliminated.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 4 is a cross-sectional view of the micropipette adaptor as seen along the line 4—4 in FIG. 2;

FIG. 5 is a schematic diagram showing a second embodiment of the micropipette adaptor in its operative relationship with elements of a spectrofluorimeter; and FIG. 6 is a schematic diagram showing a third embodiment of the micropipette adaptor in its operative relationship with elements of a spectrophotometer or spectrofluorimeter.

DESCRIPTION OF THE PREFERRED EMBODIMENT

Figure 1:
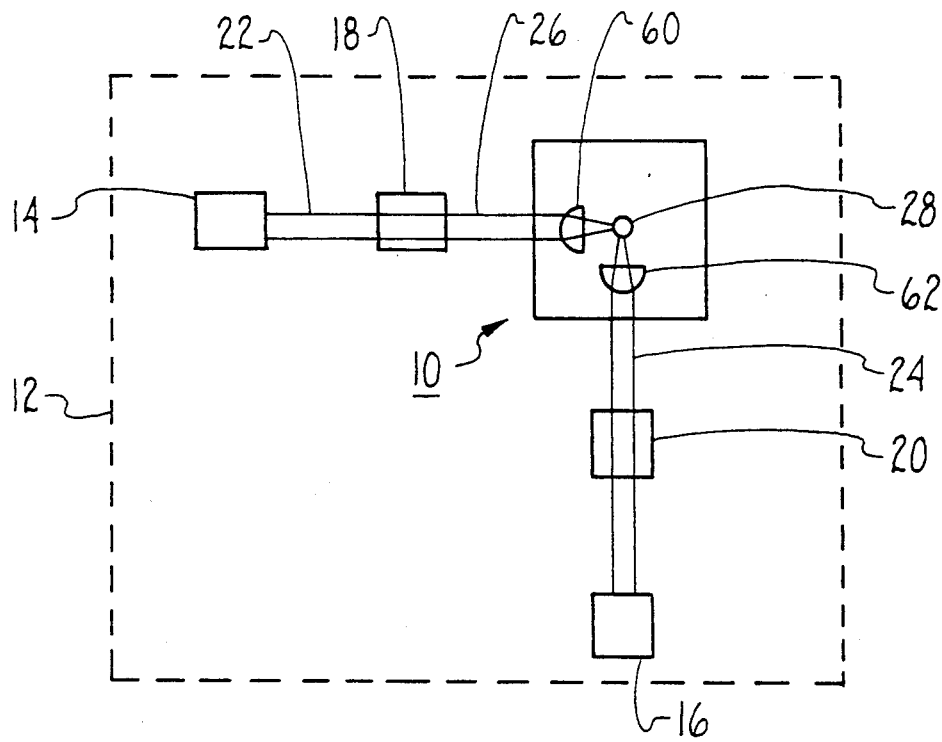
FIG. 1 is a schematic diagram showing a first embodiment of the micropipette adaptor in its operative relationship with elements of a spectrofluorimeter.

Referring initially to FIG. 1, a micropipette adaptor, generally designated 10, is shown in operative engagement with a spectrofluorimeter 12, shown in phantom, the adaptor 10 being positioned between a light source 14 and a detector 16. Light source 14 is any suitable source of visible infrared or ultraviolet light which has sufficient energy to excite sample molecules contained in adaptor 10 to higher energy states. In addition, variable monochromer 18 is shown positioned in the path of light beam 22, to pass light from light source 14 of a selected wavelength. As so positioned, a beam of collimated or approximately collimated light 22 from light source 14 is filtered by monochromer 18, whereupon monochromatic beam 26 is directed to impinge upon micropipette 28 with a known intensity and wavelength. In a manner to be subsequently disclosed, lens 60 of micropipette adaptor 10 focuses the collimated, monochromatic beam 26 onto the micropipette 28 which is held by the adaptor 10. When so irradiated by beam 26, the molecules of the substance contained in micropipette 28 are excited to higher quantum energy states. As is well known in the pertinent art, molecules so excited may de-excite by reverting to their ground energy state, thereby emitting one or more photons of known wavelengths by the processes known as fluorescence or phosphorescence. Fluorescent or phosphorescent radiation so emitted is recollimated by lens 62 of adaptor 10 into output light beam 24, which has a given intensity and wavelength (or wavelengths). Variable monochromer 20 may be positioned in the beam 24, as shown, to pass only photons which have a preselected wavelength. As will be appreciated by the skilled artisan, the concentration of the substance held by micropipette 28 may be determined by evaluating the difference in intensity between light beams 24 and 26, while the nature and composition of the substance may be analyzed by observing the wavelength(s) of fluorescent light beam 24.

Figure 2:
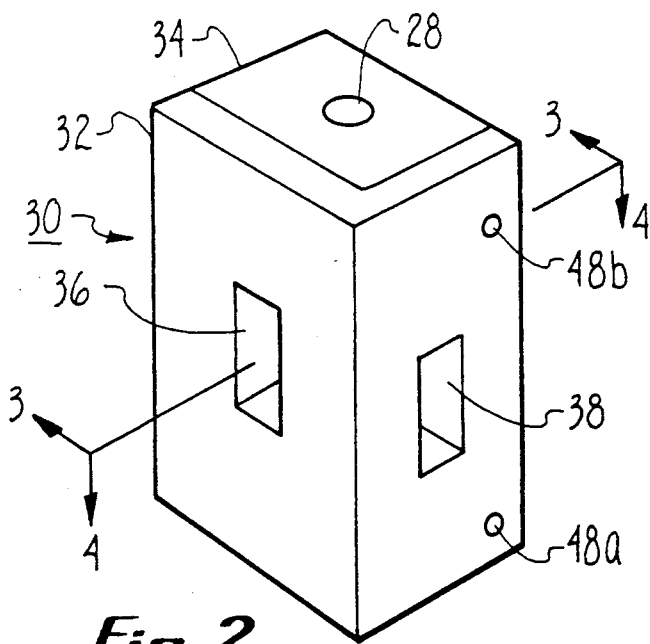
FIG. 2 is a perspective view of the micropipette adaptor with selected portions broken away for clarity.

The construction of micropipette adaptor 10 is best seen in FIG. 2, which shows a base generally designated 30. In particular, while base 30 may comprise a single structure, in accordance with the embodiment shown base 30 comprises lens housing 32 and micropipette housing 34. The housings 32 and 34 may be attached by any suitable means, such as by the screws 48a and b. Preferably, base 30 is made of a rigid, light absorbing material, such as black delrin plastic. In order to provide a capability to heat the substance contained in micropipette 28, however, base 30 may alternatively be made of a thermal conductor, such as copper or brass, to heat micropipette 28 in cooperation with a heating-/cooling source. Co-pending U.S. patent application Ser. No. 407,539, which is assigned to the same assignee as the present invention and which is a continuation-in-part of co-pending U.S. patent application Ser. No. 377,476, discloses one suitable micropipette 28 heating arrangement. For purposes of the present invention, lens housing 32 is formed with an opening 36 to allow the passage of light through housing 32 and to micropipette 28. In addition, a second opening 38 is formed in lens housing 32 to permit the passage of fluorescent light emitted by the substance contained in micropipette 28 through housing 32.

Figure 3:
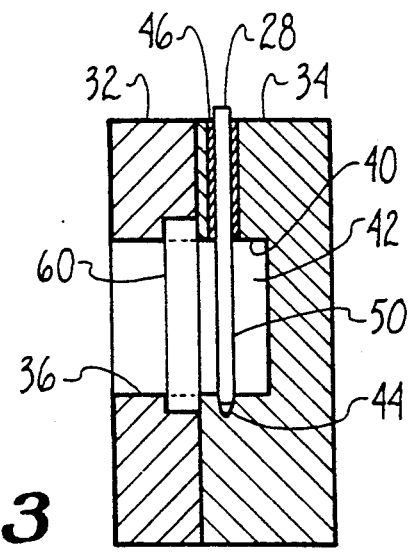
FIG. 3 is a cross-sectional view of the micropipette adaptor as seen along the line 3—3 in FIG. 2 while supporting a micropipette.

Now referring to FIG. 3, it will be seen that micropipette housing 34 is formed with an opening 40 which, for purposes stated above, is positioned in alignment with opening 36 of lens housing 32. In addition, micropipette housing 34 is formed with a passage 42 and a conical-shaped well 44 which are positioned across the opening 40 from each other. More particularly, passage 42 and well 44 receive micropipette 28 to hold micropipette 28 in place within and across opening 40. Furthermore, a bushing 46, which is appropriately sized to receive micropipette 28, may be positioned in passage 42 to securely hole micropipette 28 on adaptor 10. Bushing 46 may not be needed if precision hole is made in micropipette housing 34 to exactly fit the micropipette in use. In addition to the above structure, the skilled artisan will readily appreciate that micropipette housing 34 is also formed with an opening (not shown) which is aligned with the opening 38 of lens housing 32.

As is to be appreciated, portion 50 of micropipette 28, which is that portion of the micropipette that extends across opening 40, is the portion of micropipette 28 that is irradiated by light from source 14. It will therefore be appreciated that the housings 32 and 34 are positioned relative to each other such that incident light beam 26 may pass directly through the openings 36, 40, and emitted light beam 24 may pass across opening 40 and through opening 38.

Now referring to FIG. 4, a lens 60 is shown positioned in opening 36. Specifically, lens 60 is attached or mounted on housing 32 by any means well known in the pertinent art, such as by gluing, press fitting, or solvent bonding. Further, lens 60 may be mounted on housing 32 by a frictional snap-in configuration or held thereon by set screws (not shown). Similarly, a lens 62 is attached or mounted on housing 32 and is positioned in the opening 38 substantially as shown. For purposes of the present invention, it is preferable that the lenses 60, 62 by cylindrical. This is so in order for the lens 60 (the directing lens) to linearly focus input light beam 26 onto a line which can be positioned along the longitudinal axis of micropipette 28. More particularly, lens 60 should be positioned to focus beam 26 in a line that is substantially as wide as the lumen of micropipette 28, which for the embodiment shown, is approximately one half millimeter (0.5 mm). Further, a cylindrical shape for lens 62 (the receiving lens) is also preferable in order for fluorescent light emitted by the substance contained in micropipette 28 to be collimated as output light beam 24. Preferably, both cylindrical lens 60 and cylindrical lens 62 are made of a quartz material which permits use of either visible or ultraviolet light, although other materials, such as sapphire, may be suitable depending on the wavelength of beam 26.

Importantly, lenses 60, 62 are positioned in housing 32 such that their respective lens axes 66, 68 are substantially perpendicular to each other. Moreover, the lenses 60, 62 are positioned to be substantially co-planar with irradiated portion 50 of micropipette 28. This is so because, as is well known in the art, fluorescent or phosphorescent radiation from the substance contained within micropipette 28 will be emitted substantially isotopically relative to micropipette 28. It is the case, however, that by collimating for processing only emitted fluorescent or phosphorescent light which is perpendicular relative to the direction of the irradiating light, the amount of non-fluorescent light reaching the detector is minimized. For example, it is undesirable that photons in irradiating beam 26 reach detector 16 (shown in FIG. 1A). Such direct radiation will be understood to cause false readings by detector 16. Thus, by so disposing lenses 60, 62 substantially perpendicularly, the amount of non-fluorescent and non-phosphorescent light impinging on detector 16 is minimized. On the other hand, the amount of fluorescent and phosphorescent light available for detection is geometrically maximized by placing the lenses 60, 62 and portion 50 in co-planarity, as disclosed above. Thus, when lenses 60, 62 are disposed as disclosed, the relatively higher intensity of fluorescent light beam 24 which irradiates detector 16 increases the accuracy and precision of the detector 16 output signal. Further to this objective, walls 56 of opening 40 may be composed of a black, light absorbing material such as black delrin plastic or anodized copper. Finally, it will be appreciated by the skilled artisan that the lenses 60, 62 are positioned within housing 32 such that their respective focal points are substantially coincident with the longitudinal axis of micropipette 28, for reasons disclosed above.

FIGS. 5 and 6 show alternative embodiments of micropipette adaptor 10 which recognize the fact that other applications of adaptor 10, in addition to the ones above, may be provided for in a single embodiment. For example, FIG. 5 shows a micropipette adaptor 70 in which an external light source and a directing lens have been eliminated. As the skilled artisan will appreciate such an embodiment of micropipette adaptor 70 is useful for analyzing radiation spontaneously emitted by chemiluminescent or bioluminescent substances which may be contained in micropipette 28. Alternatively, the micropipette adaptor 72 shown in FIG. 6 provides for analysis by spectrophotometry, in addition to providing for chemiluminescence, bioluminescence, and spectrofluorescence analysis capabilities. Specifically, the micropipette adaptor 72 of FIG. 6 contemplates the incorporation of a directing lens 74, a spectrofluorescent receiving lens 76, and a spectrophotometric receiving lens 78. In the embodiment shown, the lenses 74, 76 are positioned within adaptor 72 in substantially the same manner as the lenses 60, 62 are disposed in adaptor 10 in FIG. 1, as disclosed above. Thus, the lenses 74, 76 in combination provide for analysis by spectrofluorimetry. In addition, spectrophotometric receiving lens 78 is substantially diametrically opposed to directing lens 74 within adaptor 72 and, in combination with lens 74, provides for analysis by spectrophotometry in a manner disclosed in co-pending application No. 407,539, referenced earlier. Finally, micropipette adaptor 72 may include shields 80, 82, and 84 for lenses 74, 76 and 78, respectively. Shields 80, 82, and 84 are any suitable light shields which are removeably disposed on adaptor 72 to prevent visible or ultraviolet light from passing freely through the affected lens between micropipette 28 and other components of adaptor 72. For example, when it is desired to use adaptor 72 for spectrofluorimetry, shield 84 is positioned adjacent lens 78 to prevent unwanted radiation from entering adaptor 72 through lens 78. Similarly, to use adaptor 72 for a spectrophotometric application, shield 82 is positioned adjacent lens 76. Finally, to use adaptor 72 in a chemiluminescent or bioluminescent application, lenses 74 and 78 are functionally removed from adaptor 72 by positioning shields 80, 84 to block light from passing through their respective lenses.

It is also possible to use the embodiment shown in FIG. 6 to make spectrophotometric and spectrofluorimetric measurements simultaneously. The simultaneous measurement could allow for substantial improvement over making the measurements separately. An increased accuracy in measurements is possible in spectrophotometry because scattered or fluorescent light can be monitored independently thru lens 76. An increased accuracy is possible in spectrofluorimetric measurements because the light monitored thru lens 78 can be used to more precisely measure the light which passed thru the sample.

While the particular micropipette adaptor for spectrofluorimeters as herein shown and disclosed in detail is fully capable of obtaining the objects and providing the advantages herein before state, it is to be understood that it is merely illustrative of the presently preferred embodiments of the invention and that no limitations are intended to the details of construction or design herein shown other than as defined in the appended claims.

I claim:

1. An adaptor for holding in a spectrofluorimeter an elongated micropipette which contains chemiluminescent or bioluminescent matter and which comprises:
    a base adapted to hold said micropipette; and
    an elongated, substantially cylindrical focussing lens disposed on said base with said lens elongation substantially aligned with said micropipette elongation for collimating light emitted from said micropipette for measurement by said spectrofluorimeter.

2. An adaptor for holding in a spectrofluorimeter an elongated micropipette which contains chemiluminescent or bioluminescent matter as recited in claim 1 wherein said collimating means is a cylindrical quartz lens.

3. An adaptor for holding in a spectrofluorimeter an elongated micropipette which contains chemiluminescent or bioluminescent matter as recited in claim 1 wherein said base is formed with a hole and a substantially conical well adjacent said hole, said conical well being aligned with said hole and cooperating with said hole to hold said micropipette.

4. An adaptor for holding in a spectrofluorimeter an elongated micropipette which contains chemiluminescent or bioluminescent matter as recited in claim 1 further comprising a bushing disposed in said hole to securely hold said micropipette on said base.

5. An adaptor for holding in a spectrofluorimeter an elongated micropipette which contains chemiluminescent or bioluminescent matter as recited in claim 1 wherein said base is made of black, light absorbing material.

6. An adaptor for holding in a spectrofluorimeter an elongated micropipette which contains chemiluminescent or bioluminescent matter as recited in claim 1 wherein said base is made of thermal conducting material.

7. An adaptor for holding in a spectrofluorimeter an elongated micropipette which contains chemiluminescent or bioluminescent matter as recited in claim 1 wherein said light is electromagnetic radiation substantially in the ultraviolet or visible spectrum.

8. An adaptor for holding an elongated micropipette in a spectrofluorimeter having a source of collimated light which comprises:
    a base for holding said micropipette;
    a directing lens for linearly focussing the collimated light from said light source substantially along the longitudinal axis of said micropipette, said light having a first direction; and
    a receiving lens for recollimating light which is emitted from said micropipette in a direction substantially perpendicular to said first direction for measurement of said emitted light by said spectrofluorimeter.

9. An adaptor for holding an elongated micropipette in a spectrofluorimeter having a source of collimated light as recited in claim 8 wherein said lenses are substantially cylindrical quartz masses.

10. An adaptor for holding an elongated micropipette in a spectrofluorimeter having a source of collimated light as recited in claim 8 wherein said base is formed with a hole and a substantially conical well adjacent to said hole, said conical well being aligned with said hole and cooperating with said hole to hold said micropipette.

11. An adaptor for holding an elongated micropipette in a spectrofluorimeter having a source of collimated light as recited in claim 8 further comprising a bushing disposed in said hole to securely hold said micropipette on said base.

12. An adaptor for holding an elongated micropipette in a spectrofluorimeter having a source of collimated light as recited in claim 8 wherein said base comprises a black, light-absorbing material.

13. An adaptor for holding an elongated micropipette in a spectrofluorimeter having a source of collimated light as recited in claim 8 wherein said base comprises a thermal conducting material.

14. An adaptor for holding an elongated micropipette in a spectrofluorimeter having a source of collimated light as recited in claim 8 wherein said light is electromagnetic radiation substantially in the ultraviolet or visible spectrum.

15. An adaptor for holding an elongated micropipette in a spectrofluorimeter having a source of collimated light as recited in claim 8 further comprising means for shielding said directing lens from said light source.

16. An adaptor for holding an elongated micropipette in a spectrofluorimeter having a source of collimated light as recited in claim 9 wherein the position of said directing lens relative said light source defines a first lens focal axis, said first lens focal axis further defining said first direction; and
    said receiving lens defines a second lens focal axis, said receiving lens being disposed in said adaptor to establish said second lens focal axis to be disposed substantially in said second direction.

17. An adaptor for holding an elongated micropipette in a spectrofluorimeter having a source of collimated light as recited in claim 16 wherein said first and second lens focal axes define a plane that is substantially perpendicular to the longitudinal axis of said micropipette.

18. An adaptor for holding a micropipette in a spectrophotometer or spectrofluorimeter having a source of collimated light which comprises:
    a base for holding said micropipette;
    directing means for linearly focussing the collimated light from said light source along the longitudinal axis of said micropipette, said light having a first direction;

spectrophotometric receiving means for recollimating light which emerges from said micropipette in a direction substantially parallel to said first direction, for measurement of said parallel emergent light by said spectrophotometer; and spectrofluorescent receiving means for recollimating light which emerges from said micropipette in a direction substantially perpendicular to said first direction, for measurement of said perpendicular emergent light by said spectrofluorimeter.

19. An adaptor for holding a micropipette in a spectrophotometer or spectrofluorimeter having a source of collimated light as recited in claim 18 wherein said directing means, said spectrophotometric receiving means, and said spectrofluorescent receiving means are substantially cylindrical quartz lenses.

20. An adaptor for holding a micropipette in a spectrophotometer or spectrofluorimeter having a source of collimated light as recited in claim 18 wherein said base is formed with a hole and a substantially conical well adjacent to said hole, said conical well being aligned with said hole and cooperating with said hole to hold said micropipette.

21. An adaptor for holding a micropipette in a spectrophotometer or spectrofluorimeter having a source of collimated light as recited in claim 18 further comprising a bushing disposed in said hole to securely hold said micropipette on said base.

22. An adaptor for holding a micropipette in a spectrophotometer or spectrofluorimeter having a source of collimated light as recited in claim 19 wherein said base is made of black, light absorbing material.

23. An adaptor for holding a micropipette in a spectrophotometer or spectrofluorimeter having a source of collimated light as recited in claim 19 wherein said base is made of thermal conducting material.

24. An adaptor for holding a micropipette in a spectrophotometer or spectrofluorimeter having a source of collimated light as recited in claim 19 wherein said light is electromagnetic radiation substantially in the ultraviolet or visible spectrum.

25. An adaptor for holding a micropipette in a spectrophotometer or spectrofluorimeter having a source of collimated light as recited in claim 10 further comprising means for substantially shielding said directing means from said light source.

26. An adaptor for holding a micropipette in a spectrophotometer or spectrofluorimeter having a source of collimated light as recited in claim 18 further comprising means for substantially shielding said spectrophotometric receiving means from said light source.

27. An adaptor for holding a micropipette in a spectrophotometer or spectrofluorimeter having a source of collimated light as recited in claim 18 further comprising means for substantially shielding said spectrofluorescent receiving means.

28. An adaptor for holding a micropipette in a spectrophotometer or spectrofluorimeter having a source of collimated light as recited in claim 19 wherein said directing lens defines a first lens focal axis, said first lens focal axis further defining said first direction; and said receiving lens defines a second lens focal axis, said receiving lens being disposed in said adaptor to establish said second lens focal axis to be disposed substantially in said second direction.

29. An adaptor for holding a micropipette in a spectrophotometer or spectrofluorimeter having a source of collimated light as recited in claim 28 wherein said lenses are coplanar and said first and second lens focal axes intersect in a line that is substantially coincident with said longitudinal axis of said micropipette.

30. A method for determining the light emission characteristics of a substantially minute sample solution held in a micropipette which comprises the steps of:
producing a beam of collimated light;
positioning said micropipette in the path of said beam;
linearly focussing said beam into axial alignment with said micropipette;
recollimating light which emerges from said micropipette substantially perpendicular to said path of said beam; and
measuring the recollimated light to determine the light emission characteristics of said sample.

31. A method for simultaneously determining the light emission and light absorption characteristics of a sample solution held in a micropipette comprising:
producing a beam of light;
positioning said micropipette in the path of said beam;
directing said beam into axial alignment with said micropipette;
measuring the light to determine the light emission characteristics of said sample; and
measuring the light which emerges from said micropipette substantially parallel to said path of said beam to determine the light absorption characteristics of said sample.

32. A method for simultaneously determining the light emission and light absorption characteristics of a sample solution held in a container as recited in claim 31 wherein said producing step comprises producing a beam of collimated light, and said directing step comprises linearly focussing said collimated beam into axial alignment with said micropipette; and further comprising the steps of:
collimating light which emerges from said micropipette substantially perpendicular to said path of said collimated beam to determine the light emission characteristics of said sample; and
recollimating light which emerges from said micropipette substantially parallel to said path to determine the light absorption characteristics of the sample.

* * * * *